United States Patent [19]

Cannon et al.

[11] Patent Number: 5,085,864
[45] Date of Patent: Feb. 4, 1992

[54] INJECTABLE FORMULATION FOR LIPOPHILIC DRUGS

[75] Inventors: John B. Cannon, Grayslake; Chung-Chiang Hsu, Libertyville; Karen J. Papp, Waukegan; N. Adeyinka Williams, Vernon Hills, all of Ill.

[73] Assignee: Abbott Laboratories, Abbott Park, Ill.

[21] Appl. No.: 704,656

[22] Filed: May 20, 1991

Related U.S. Application Data

[63] Continuation of Ser. No. 428,803, Oct. 30, 1989, abandoned.

[51] Int. Cl.5 ............................................. A61K 37/22
[52] U.S. Cl. ..................................... 424/450; 424/422
[58] Field of Search ................. 424/422, 450; 435/177

[56] References Cited

U.S. PATENT DOCUMENTS

| | | | |
|---|---|---|---|
| 4,158,707 | 6/1979 | Steffen et al. | 424/244 |
| 4,342,826 | 8/1982 | Cole | 435/177 |
| 4,731,210 | 3/1988 | Weder et al. | 424/450 |
| 4,882,164 | 11/1989 | Ferro et al. | 424/450 |

*Primary Examiner*—Thurman K. Page
*Assistant Examiner*—Donald R. McPhail
*Attorney, Agent, or Firm*—Andreas M. Danckers; Steven F. Weinstock

[57] ABSTRACT

An injectable drug composition including a therapeutically effective amount of a lipophilic drug and a bile salt.

9 Claims, No Drawings

INJECTABLE FORMULATION FOR LIPOPHILIC DRUGS

This application is a continuation of U.S. application Ser. No. 07/428,803, filed on Oct. 30, 1989, now abandoned.

TECHNICAL FIELD

This invention relates to an injectable composition for lipophilic drugs.

BACKGROUND ART

Lipophilic drugs are not administered by intramuscular injection or intravenous infusion because severe pain ensues at the injection site. A variety of approaches have been taken to address this problem. For example, attempts have been made to overcome this problem by derivatizing these druqs. Further, fat emulsion formulations have been developed; however, drug solubility has been a problem with such formulations. Accordingly, there is a continuing need for injectable compositions of lipophilic drugs that do not cause severe pain at the injection site.

SUMMARY OF THE INVENTION

The present invention relates to an injectable composition comprised of a lipophilic drug incorporated into micelles of a bile salt. The compositions of the present invention may also contain stabilizers, preservatives and other emulsifiers. Typical drugs which benefit from such compositions include macrolide antibiotics such as erythromycin and clarithromycin.

DETAILED DESCRIPTION OF THE INVENTION

The pharmaceutical compositions of the present invention comprise an intravenous formulation of a lipophilic drug in which the drug is incorporated into micelles of a bile salt at neutral pH. The composition can be administered by central or peripheral venous routes.

By "lipophilic drug" as used herein is meant drugs having an affinity for fat. Lipophilic drugs include erythromycin base and its pharmaceutically acceptable salts and esters, as well as the semisynthetic derivatives of erythromycin, including but not limited to 6-O-methyl-erythromycin (clarithromycin), the erythromycin 9-oximes, erythromycin 11, 12-cyclic carbamates and 4''-deoxy-11, 12 carbamates, 1-0-methyl-, and 6, 11-di-O-methyl erythromycins, 8-fluoroethyromycin, erythromycin 4''-carbamates, and compounds having various combinations of these structural modifications, as well as their pharmaceutically acceptable salts and esters.

The preferred lipophilic druqs for use in this invention are erythromycin, clarithromycin, and the pharmaceutically acceptable salts and esters thereof.

By "pharmaceutically acceptable salts and esters" as used herein is meant those salts and esters which are, within the scope of sound medical judqment, suitable for use in contact with the tissues of humans and lower animals without undue toxicity, irritation, allergic response, and the like, commensurate with a reasonable benefit/risk ratio, and effective for their intended use in the chemotherapy and prophylaxis of antimicrobial infections. Among the more common pharmaceutically acceptable salts and esters of macrolide antibiotics are the acetate, estolate (lauryl sulfate salt of the propionate ester), ethyl succinate, gluceptate (glucoheptonate), lactobionate, stearate, and hydrochloride forms. Other acid salts used in the pharmaceutical arts are the following: adipate, alginate, aspartate, benzoate, benzene sulfonate, bisulfate, butyrate, citrate, camphorate, camphorsulfonate, cyclopentanepropionate, digluconate, dodecylsulfate, ethanesulfonate, fumarate, gluconate, glycerophosphate, hemisulfate, heptonate, hexanoate, hydrobromide, hydroiodide, 2-hydroxy ethanesulfonate, lactate, maleate, methanesulfonate, 2-naphthalenesulfonate, nicotinate, oxalate, pamoate, pantothenate, pectinate, persulfate, 3-phenylpropionate, picrate, pivalate, propionate, succinate, tartrate, thiocyanate, tosylate, and undecanoate. Basic nitrogen-containing groups can be quaternized with such agents as lower alkyl halides, such as methyl, ethyl, propyl and butyl chloride, bromides and iodides; dialkyl sulfates like dimethyl, diethyl, dibutyl, and diamyl sulfates; long chain halides such as decyl, lauryl, myristyl and stearyl chlorides, bromides and iodides; aralkyl halides like benzyl and phenethyl bromides and others. Water or oil-soluble or dispersible products are thereby obtained.

As used herein the term "bile salts" includes salts of bile acid, i.e. steroids having 1-3 hydroxyl groups and a five carbon atom side chain terminating in a carboxyl group, which can be conjugated to glycine or taurine. Bile salts include cholate, deoxycholate, chenodeoxycholate, or ursodeoxycholate, and their qlycine or taurine conjugates, e.g. glycodeoxycholate (GDC), glycocholate (GC), or taurodeoxycholate (TDC).

The formulation of the present invention can be prepared so that it is ready-to-use or can be prepared as a lyophilized powder that can be reconstituted at a later date and diluted before use.

Generally, the formulation of the present invention can be prepared by dissolving the drug and bile salt, at low pH, along with other desired ingredients such as polyvinylpyrrolidone, albumin, phosphate buffer and dextrose. The pH can then be adjusted to pH 7-8 and, if desired, the sample can be lyophilized, stored, and reconstituted at a later date, immediately before use.

Alternatively, the drug and bile salt are dissolved in an organic solvent and the organic solvent is evaporated off. The residue is reconstituted in water (buffered to pH 7-8) containing 0-5% propylene glycol or 0-5% dextrose, and shaken to dissolve.

Typical formulations will include 2-30 mg/ml of clarithromycin (5 mg/ml preferred) and 9-65 mg/ml of bile salt. Minimum concentrations for solubilization of the drug at neutral pH are: GDC (2.5 moles /mole of drug) TDC: (4 moles/mole of drug); the ratio (mole/mole) of bile salt to drug can be 2.5-25 (for GDC) and 4-25 (for TDC).

The formulation can also contain stabilizers and/or preservatives. These include polyvinylpyrrolidone (PVP) (0-5%), propylene qlycol (0-5%); dextrose (0-5%).

Bile salts are known to be hemolytic agents. Therefore, it is desirable to include substances which prevent or retard the extent of hemolysis arising from the formulation, such as human serum albumin (2.5-7.5%). Mixed micellar systems, such as bile salt-phosphatidyl choline clarithromycin systems may be advantageous, since mixed micelles of bile salts and phospholipids are less hemolytic, less toxic than bile salts alone, and more stable than bile salt albumin-clarithromycin formulations.

Mixed micelle systems include mixtures of bile salts (cholate, deoxycholate, glycocholate, glycodeoxycholate, or GDC/GC combinations) and phospholipids. The phospholipids include purified preparations of egg or soybean phosphatidyl choline (PC); crude preparations of egg or soybean phospholipids; or synthetic phospholipids (e.g., dimyristoyl or dipalmitoyl PC). The molar ratio of bile salt to phospholipid should be greater than 1 to insure visual clarity of the solution and less than 3 to decrease hemolysis. Phosphatidic acid or other negatively charged lipids can be included to increase the stability of the clarithromycin-phospholipid-bile salt micelle.

The following examples are intended to illustrate the invention without limiting the practice thereof.

EXAMPLES 1-5

EXAMPLE 1: Clarithromycin (20 mg), polyvinylpyrrolidone (PVP) (100 mg) and sodium taurocholate (100 mg) were dissolved in 5 ml methylene chloride/methanol (1:1), and the solvent evaporated off by an air stream. The mixture was reconstituted in 4 ml of 2.5% propylene glycol and 0.01M sodium phosphate, pH 7.5, to give a clear solution. Physical stability is ca. 1 hour (i.e., precipitation of drug was observed within one hour).

EXAMPLE 2: Clarithromycin (25 mg), PVP (250 mg) and sodium taurodeoxycholate (125 mg) were dissolved in 2.5 ml of 0.1M acetate buffer (pH 4.5); 250 mg of propylene glycol was added. The pH was adjusted to 7 with dilute NaOH and brought to 5 ml with water. Physical stability is >3 months (i.e., no precipitation was observed after storage of up to 3 months).

EXAMPLE 3: Same as Example 2, but with no PVP or propylene glycol. Physical stability is >3 months.

EXAMPLE 4: To 5 ml of a 50 mg/ml solution of clarithromycin lactobionate (0.333 mmole) is added 869 mg (1.67 mmole) of TDC and ca. 20 ml of 5% dextrose. After the bile salt is dissolved, the pH is adjusted to 7.5 with dilute NaOH, and the final volume brought to 50 ml with 5% dextrose.

EXAMPLE 5: Same as Example 4, but with 472 mg (1.0 mmole) of GDC instead of TDC. Optionally, this formulation can be lyophilized and reconstituted with no loss of stability.

SCRATCH TEST

A scratch test was conducted in mice to measure the response to the sensation of irritation, i.e., the pain associated with an injection. Formulations were administered subcutaneously at a dose of 5 ml/kg to groups of mice (10/group) weighing 20 to 40 g each. The number of times that each mouse scratched the injection site was then counted for exactly five minutes. The results are summarized in Table I below.

TABLE I

| | Mouse Scratch Test | |
|---|---|---|
| Example | Formulation (molar ratios) | No. of Scratches |
| 1 | C/TC 1:7 + 2.5% PVP + 2.5% PG | 6 ± 8 |
| 2 | C/TDC 1:7.2 + 5% PVP + 5% PG | 9.3 ± 3.4 |
| 3 | C/TDC 1:7.2 | 12.5 ± 8.9 |
| 4 | CL/TDC 1:5 | 8.2 ± 5.3 |
| 5 | CL/GDC 1:3 | 6.8 ± 4.5 |
| Controls: | | |
| Saline (0.85%) | | 3 ± 2 |
| Clarithromycin Lactobionate (5 mg/ml) | | 22.0 ± 7.2 |

All formulations were 5 mg/ml in clarithromycin; abbreviations: C=clarithromycin; CL=clarithromycin lactobionate; TC=sodium taurocholate; TDC=sodium taurodeoxycholate; GDC=sodium glycodeoxycholate; PVP=polyvinylpyrrolidone; PG=propylene glycol.

EXAMPLES 6-16

Examples 6-16 were prepared by mixing b 5 mg/ml clarithromycin lactobionate and up to 3 molar equivalents of sodium glycodeoxycholate with the pH adjusted as shown. The mouse scratch test results are shown in TABLE II below.

TABLE II

| EXAMPLE | FORMULATION | NO. OF SCRATCHES |
|---|---|---|
| 6 | 3 eq GDC, pH 6.53 | 6.1 ± 3.5 |
| 7 | 3 eq GDC, 2% PG, pH 6.51 | 8.1 ± 6.3 |
| 8 | 3 eq GDC, 2.5% PVP, pH 6.54 | 10.5 ± 5.5 |
| 9 | 3 eq GDC, 2% PG, 2.5% PVP, pH 6.63 | 8.5 ± 7.3 |
| 10 | 3 eq GDC, pH 7.46 | 3.6 ± 3.0 |
| 11 | 3 eq GDC, 2% PG, pH 7.48 | 7.5 ±2.6 |
| 12 | 3 eq GDC, 2.5% PVP, pH 7.47 | 9.9 + 4.6 |
| 13 | 3 eq GDC, 2% PG, 2.5% PVP, pH 7.52 | 7.7 + 5.2 |
| 14 | 3 eq GDC, 1% PG, 1.25% PVP, pH 7.06 | 7.8 ± 4.5 |
| 15 | 2 eq GDC, 1% PG, 1.25% PVP, pH 7.01 | 9.6 ± 5.9 |
| 16 | Clarithromycin lactobionate | 15.1 ± 4.4 |

All solutions were 5 mg/ml clarithromycin; GDC=sodium glycodeoxycholate, PG=propylene glycol, PVP=polyvinylpyrrolidone.

EXAMPLES 17-18

Examples 17-18 were prepared by preparing 5 mg/ml clarithromycin lactobionate and 3 molar equivalents of sodium glycodeoxycholate with the pH adjusted to 7-7.5, as in Example 5; the appropriate volume of 25% albumin solution was added before final dilution with 5% dextrose.

EXAMPLE 19

To a solution of adipic acid (2.65 mg, 0.018 mmole) and sodium chenodeoxycholate (83 mg, 0.2 mmole) in ca. 5 ml of methanol, was added a solution of 25 mg (0.033 mmole) clarithromycin in 1 ml of methylene chloride. The solvent was evaporated with an air stream, and reconstituted with 5 ml of cold 0.05M sodium phosphate buffer, pH 7.5, and vortexed to give a clear solution.

EXAMPLE 20

As in Example 19, but with 57.8 mg (0.14 mmoles) sodium deoxycholate instead of chenodeoxycholate.

EXAMPLES 21-29

Examples 21-29 are mixed micelle formulations, prepared by modification of the organic method (Example 1) or the aqueous method (Examples 2-5), as follows:

EXAMPLE 21: To a solution of adipic acid (5.5 mg, 0.038 mmole) and sodium qlycodeoxycholate (31.4 mg, 0.067 mmole) and glycocholic acid (65.2 mg, 0.133 mmole) in ca. 4 ml of methanol was added a solution of 50 mg (0.067 mmole) clarithromycin in 2 ml of methylene chloride. The solvent was evaporated with an air stream, and reconstituted with 6.3 ml of a 2.5% solution of egg phosphatide (ca. 2 mmoles) and 2 ml of 0.25M sodium phosphate buffer, pH 7.5, and 1.7 ml of a 125 mg/ml solution of dextrose. The mixture was vortexed to give a clear solution, pH 7.4 and osmolarity 290 mOsm.

EXAMPLE 22: Clarithromycin base (250 mg, 0.33 mmoles) and egg lecithin (99% phosphatidyl choline) (440 mg, 0.57 mmole) and phosphatidic acid (230 mg, 0.30 mmole) are dissolved together in chloroform. The solvent is evaporated to leave a film of the drug/lipid mixture on the wall of the container, to which is added 50 ml of a solution of sodium chenodeoxycholate (692 mg, 1.67 mmole) in pH 7.5 0.05M sodium phosphate buffer. The mixture is shaken until the film is dissolved, resulting in a clear solution within 1-3 hours.

EXAMPLE 23: Solid egg lecithin (99% phosphatidyl choline) (235 mg, 0.30 mmole) is stirred into 25 ml of a solution of sodium cholate (720 mg, 1.67 mmole) in pH 7.5 0.1M sodium phosphate buffer until a clear solution results. This solution is combined with 25 ml of a solution of clarithromycin lactobionate (250 mg, 0.33 mmoles), and the pH adjusted to 7.5, resulting in a clear solution.

EXAMPLE 24: Egg lecithin (42 mg, 0.054 mmole) is dissolved in chloroform. The chloroform is rotary evaporated leaving a thin lipid film on the wall of the flask. The lipid film is dissolved in an aqueous solution of sodium cholate (155 mg, 0.35 mmole) and made up to 4.5 ml; 0.5 ml of an aqueous solution of clarithromycin lactobionate (25 mg, 0.033 mmole) is added to the mixed-micelle solution while stirring, resulting in a clear solution of pH 7.5.

EXAMPLE 25: As in Example 24, but with 23.6 mg (0.030 mmole) egg lecithin and 69 mg (0.17 mmole) of sodium chenodeoxycholate. Final pH is 8.1.

EXAMPLE 26: Clarithromycin base (25 mg, 0.033 mmole), egg lecithin (67 mg, 0.09 mmole), and phosphatidic acid (33 mg, 0.05 mmole) are dissolved in chloroform. The chloroform is rotary evaporated leaving a film of the lipid-clarithromycin mixture on the wall of the flask.

The film is hydrated with an aqueous solution of sodium cholate (213 mg, 0.5 mmole), stirred until the solution becomes clear and made up to 5.0 ml with water. The pH of the solution is about 7.2.

EXAMPLE 27: To 5 ml of a 50 mg/ml solution of clarithromycin lactobionate (0.333 mmole) is added 472 mg (1.0 mmole) of GDC and ca. 10 ml of water. After the bile salt is dissolved, 5.15 ml of a 10% aqueous suspension of egg phosphatides (0.66 mmoles) is added and stirred until clear. Buffer (10 ml of 0.25M sodium phosphate pH 7.5) is added, the final volume brought to 50 ml with water, and the osmolarity adjusted to ca. 310 mOsm with dextrose (ca. 1.35 gm). Physical and chemical stability were monitored for 3 months; no significant loss (<5%) in potency, measured by high performance liquid chromatography (HPLC), was observed in that period. Optionally, this formulation can be lyophilized and reconstituted with no loss of stability.

EXAMPLE 28: As in Example 27, but with 7.73 ml of the 10% egg phosphatide solution (0.1 mmole).

EXAMPLE 29: As in Example 27, but with 236 mg (0.5 mmole) GDC and 245 mg (0.5 mmole) GC.

The mouse scratch test results for Examples 17-29 are shown in Table III herein below.

TABLE III

| EXAMPLE | FORMULATION | NO. OF SCRATCHES* |
|---|---|---|
| 17 | CL/GDC 1:3 + 5 Albumin | 9.1 ± 4.2 |
| 18 | CL/GDC 1:3 + 7.5 Albumin | 9.9 ± 8.1 |
| 19 | C/Ad/CDC 1:0.55:6 | 5.1 ± 5.0 |
| 20 | C/Ad/DC 1:0.55:4 | 8.5 ± 5.6 |
| 21 | C/Ad/GDC/GC/EP 1:0.55:1:2:3 | 10.0 ± 7.0 |
| 22 | C/EL/PA/CDC 1:1.7:0.9:5 | 8.6 ± 3.5 |
| 23 | CL/EL/Ch 1:0.9:5 | 11.0 ± 4.7 |
| 24 | CL/EL/Ch 1:1.6:11 | 10.7 ± 6.1 |
| 25 | CL/EL/CDC 1:0.9:5 | 11.5 ± 4.8 |
| 26 | C/EL/PA/Ch 1:2.61.4:15 | 5.1 ± 4.1 |
| 27 | CL/EP/GDC 1:2:3 | 9.0 ± 5.9 |
| 28 | CL/EP/GDC 1:3:3 | 7.6 ± 4.2 |
| 29 | CL/EP/GDC/GC 1:2:1.5:1.5 | 8.5 ± 5.4 |

*All scratch test values are normalized to an average control value of 22 for the clarithromycin lactobionate.

Abbreviations:
GDC = Sodium Glycodeoxycholate;
C = clarithromycin;
Ad = adipate;
EP = egg phosphatides (crude);
GC = sodium glycocholate;
DC = sodium deoxycholate;
CL = clarithromycin lactobionate;
EL = egg lecithin (97% PC);
Ch = sodium cholate;
CDC = sodium chenodeoxycholate;
PA = phosphatidic acid.

ANTIBACTERIAL ACTIVITY

The antibacterial activity of 4, 1, 0.25, 0.0625, and 0.0156 mg/ml compositions of (A) clarithromycin lactobionate and 3 molar equivalents of sodium glycodeoxycholate (as in Example 5); and (B) clarithromycin lactobionate, 3 molar equivalents of sodium glycodeoxycholate and 2 molar equivalents of egg phosphatides (as in Example 27); were compared to the activity of (C) clarithromycin lactobionate in mouse protection tests. Mice were infected intraperitoneally with 100 times the $LD_{50}$ dose of Staphylococcus aureus and treated one hour after infection by injecting either (A), (B) or (C) intravenously via the tail vein. $ED_{50}$ was calculated from cumulative mortalities on the sixth day after infection. The results indicate that the efficacy ($ED_{50}$) of formulations A or B were no different from that of clarithromycin lactobionate.

This invention has been described in terms of specific embodiments set forth in detail. It should be understood, however, that these embodiments are presented by way of illustration only, and that the invention is not necessarily limited thereto. Modifications and variations within the spirit and scope of the claims that follow will be readily apparent from this disclosure, as those skilled in the art will appreciate.

What is claimed is:

1. An injectable composition containing micelles which comprise a therapeutically effective amount of a lipophilic drug selected from the group consisting of erythromycin and clarithromycin and at least one bile salt.

2. The composition of claim 1 wherein the bile salt is glycodeoxycholate.

3. The composition of claim 1 further comprising an agent which prevents or retards hemolysis.

4. The composition of claim 3 wherein the agent is selected from the group consisting of albumin and phospholipid.

5. The composition of claim 2 wherein the glycodeoxycholate is present in a molar ratio to the lipophilic drug of between about 2.5:1 and about 25:1.

6. The composition of claim 3 wherein the agent is phospholipid present in a molar ratio to the bile salt of between about 1:3 and about 1:1.

7. An injectable composition containing micelles which comprise a therapeutically effective amount of clarithromycin, glycodeoxycholate and phospholipid.

8. The composition of claim 7 wherein the clarithromycin, glycodeoxycholate and phospholipid are present in a molar ratio of about 1:3:2.

9. A method for retreating or preventing a bacterial infection comprising administering intravenously, to a patient in need of treatment, a composition containing micelles which comprise a therapeutically effective amount of a lipophilic drug selected from the group consisting of erythromycin and clarithromycin and at least one bile salt.

* * * * *

UNITED STATES PATENT AND TRADEMARK OFFICE
CERTIFICATE OF CORRECTION

PATENT NO. : 5,085,864
DATED : February 4, 1992
INVENTOR(S) : J.B. Cannon, K.J. Papp, C. Hsu, N.A. Williams It is certified that error appears in the above-identified patent and that said Letters Patent is hereby corrected as shown below:

Column 1, line 19, change "druqs" to --drugs--.

Column 1, line 59, change "judqment" to --judgment--.

Column 2, line 27, change "qlycine" to --glycine--.

Column 3, line 2, change "phosph-olipids" to --phospholipids--.

Column 4, line 7, delete "b".

Column 5, line 67, change "5 Albumin" to --5% Albumin--.
Column 5, line 68, change "7.5 Albumin" to --7.5% Alburrin--.

Column 6, line 11, change "1:2.61.4:15" to --1:2.6:1.4:15--.

Column 8, line 4, change "retreating" to --treating--.

Signed and Sealed this

Eighth Day of December, 1992

Attest:

DOUGLAS B. COMER

Attesting Officer

Acting Commissioner of Patents and Trademarks